United States Patent [19]

Moser

[11] Patent Number: Plant 6,608

[45] Date of Patent: Feb. 14, 1989

[54] HIBISCUS PLANT NAMED VISTA

[75] Inventor: Frank C. Moser, Alva, Fla.

[73] Assignee: Yoder Brothers, Inc., Barberton, Ohio

[21] Appl. No.: 52,434

[22] Filed: May 21, 1987

[51] Int. Cl.[4] ..... A01H 5/00

[52] U.S. Cl. ..... Plt./54

[58] Field of Search ..... Plt./54

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Hibiscus plant named Vista particularly characterized by its cartwheel completely overlapped single flower form, dark pink flower color with a dark red eye, ruffled petal margin, heart shaped, medium sized leaves, compact growth, flower life of a single day, excellent shipping ability, and ease of rooting cuttings.

3 Drawing Sheets

The present invention comprises a new and distinct cultivar of Hibiscus, botanically known as *Hibiscus rosa-sinensis* L., and referred to by the cultivar name Vista.

Vista, identified as 83004001 during the breeding and selection process, was originated by Frank C. Moser from a planned cross hybridization between two selected breeding lines in a controlled breeding program.

The female or seed parent is an unnamed cultivar designated as code #0012 and the pollen or male parent is an unnamed cultivar designated as code #0004.

Vista was discovered and selected as a flowering plant within the progeny of the stated cross by Frank C. Moser in October of 1983, outside in cultivated ground beds in Fort Myers, Fla.

The first asexual reproduction of Vista was accomplished when vegetative cuttings were taken from the initial plant selection in November of 1983 in Fort Myers, Fla. from plants grown outside in ground beds, by technicians working under formulations established and supervised by Frank C. Moser.

Horticultural examinations of controlled flowerings of successive generations of plants derived from cuttings taken from the original selection have shown that the unique combination of characteristics as herein disclosed for Vista are fixed and retained through successive generations of asexual reproduction.

Vista has not been observed under all possible environmental conditions. The phenotype may vary significantly with variation in environment such as temperature, light intensity and fertilizer regime.

The following observations, measurements and comparisons describe plants that were grown in Fort Myers, Fla. in a controlled greenhouse environment and following a commercial schedule.

The following traits have been repeatedly observed and are determined to be basic characteristics of Vista, which, in combination, distinguish this Hibiscus as a new and distinct cultivar:

1. Cartwheel, completely overlapped single flower form.
2. Dark pink flower color with a dark red eye.
3. Ruffled petal margin.
4. Heart shaped, medium sized leaves.
5. Compact growth, requiring small amounts of growth regulator.
6. Flower life is a single day.
7. Excellent shipping ability.
8. Ease of rooting.

The accompanying photographic drawings show typical plant habit and flower and leaf characteristics of Vista, with colors being as nearly true as possible with illustrations of this type. Sheet 1 is a color photograph of Vista grown as a commercially finished pot plant. Sheet 2 is a color photograph illustrating the distinctive characteristics of the upper and lower surfaces of the flower. Sheet 3 is a color photograph showing the variation in leaf shape that can characteristically be found on any one plant of Vista.

Of the commercial cultivars known to the inventor, the most similar in comparison to Vista is the cultivar Pink Versicolor. Vista is similar to Pink Versicolor in that both produce a dark pink single flower with a red eye, are easily rooted, respond to small quantities of growth regulator, and are easy to bud.

Vista differs from Pink Versicolor in that its flowers are somewhat ruffled, its foliage is heart-shaped, not holly-shaped as in Pink Versicolor, and Vista is much more compact than Pink Versicolor.

In the following description, color references are made to The Royal Horticultural Society Colour Chart. The color readings were taken from greenhouse grown plants on Jan. 28, 1987. All readings were taken in an office under cool white florescent lights, facing a west window between the hours of 10:00 a.m. and 2:00 p.m.

Classification:

*Botanical.*—*Hibiscus rosa-sinensis* L. cv. Vista.

*Commercial.*—Greenhouse pot crop.

INFLORESCENCE

A. Flower (general):

*Size.*—Medium, 14 cm.

*Borne.*—In axils of leaves, 1 per node.

*Form.*—Cartwheel, overlapped single.

*Life.*—1 day.

*Fragrance.*—None.

*Blooming habit.*—Continuously, year round.

B. Corolla (petals):

*Texture.*—Smooth.

*Substance.*—Thick, heavy.

*Shape.*—Rounded, slight undulate margin.

*Color (fully open).*—Upper surface: base color dark pink 52A; eye, dark red 53A. Lower surface: left ¼ of petal, peach 38B; right ¾ of petal, dark pink 54A.

C. Bud (1 day prior to opening):

*Size.*—7 cm.

*Shape.*—Cylindrical, somewhat like an elongate rosebud.

*Color.*—Reddish pink 47A interspersed with veins of white shading to yellow green 154C.

D. Calyx: Cup shaped, 5 pointed lobes, a single prominent midvein per lobe, membranous.

*Length.*—2.5 cm.

*Color.*—Yellowish green 144B.

E. Epicalyx: 6–8 pointed, narrow, sword-shaped bracts.

*Length.*—1.5 cm.

*Color.*—Dark green 137A.

F. Peduncle:

*Length.*—4.5 cm.

*Strength.*—Strong.

*Aspect.*—Smooth.

*Color.*—Yellowish green 144A.

G. Reproductive structures:

(1) *Androecium* (*stamens*).—Anthers: Numerous, Color (undehicsed) peach 29B. Filaments: Length 1.0 cm, Color reddish pink 51A. Pollen: Abundant, Color yellow 15A. Staminal column: Length 7.5 cm, Color reddish pink 51A, Upper 30% antheriferous.

(2) *Gynoecium* (*pistil*).—Stigma: 5 in number, rounded, discoid, hairy. Color: Red 51A, diameter 3 mm. Style: Length 8.5 cm, Color red 51A. Branches: 5 in number, Color white. Ovary: Rounded, Color yellowish green 150B.

PLANT CHARACTERISTICS

A. Foliage:

*Arrangement.*—Alternate.

*Shape.*—Juvenile: Heterophyllus. Mature: Entire, cordate, heart shaped, serrated edge. Color: Dark green 139A.

*Petiole.*—Length 3.0–4.0 cm, Aspect smooth. Color: Green 143A.

*Stipules.*—2 per node, Shape acicular (needle shaped). Color: Green 143A.

B. Stems: Aspect smooth, becoming woody with age.

C. Plant habit: Compact.

D. Breaking action: Good.

E. Rooting: Good.

F. Growth regulator: Very little required.

G. Low light bud initiation: Poor.

H. Shipping tolerance: Good.

I claim:

1. A new and distinct cultivar of *Hibiscus rosa-sinensis* named Vista, as described and illustrated, and particularly characterized as to uniqueness by the combined characteristics of cartwheel, completely overlapped single flower form, dark pink flower color with a dark red eye, ruffled petal margin, heart shaped, medium sized leaves, compact growth, flower life of a single day, excellent shipping ability, and ease of rooting cuttings.

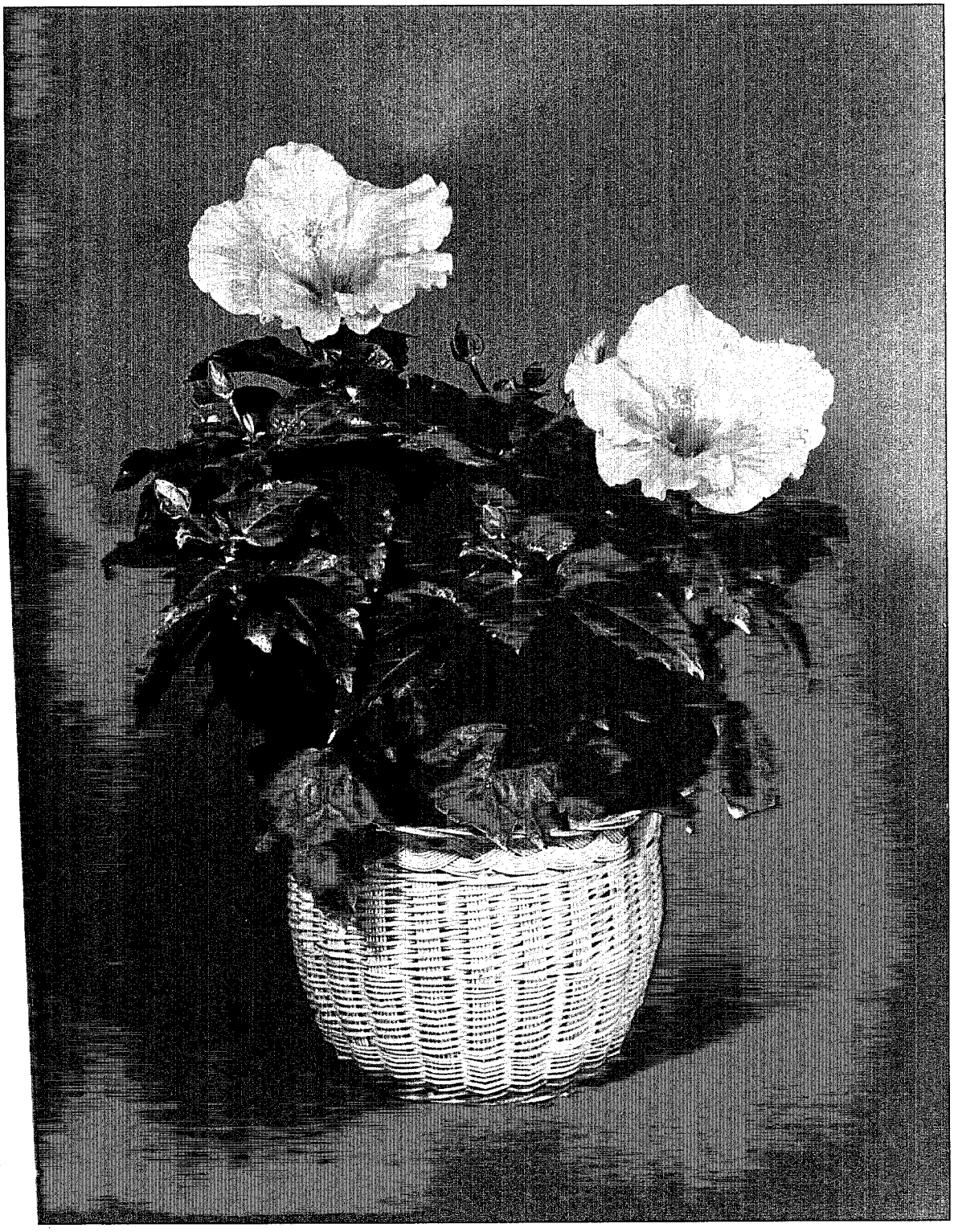

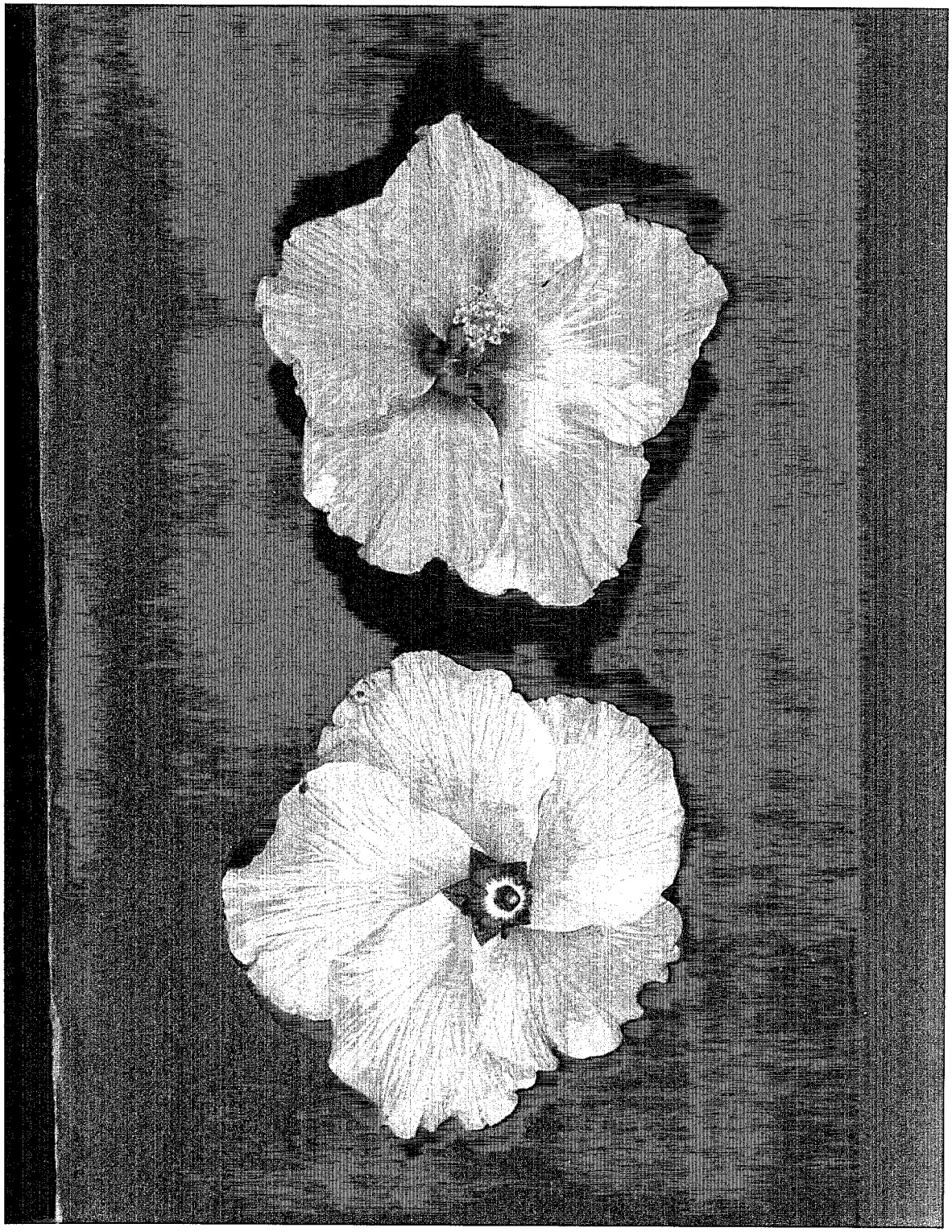

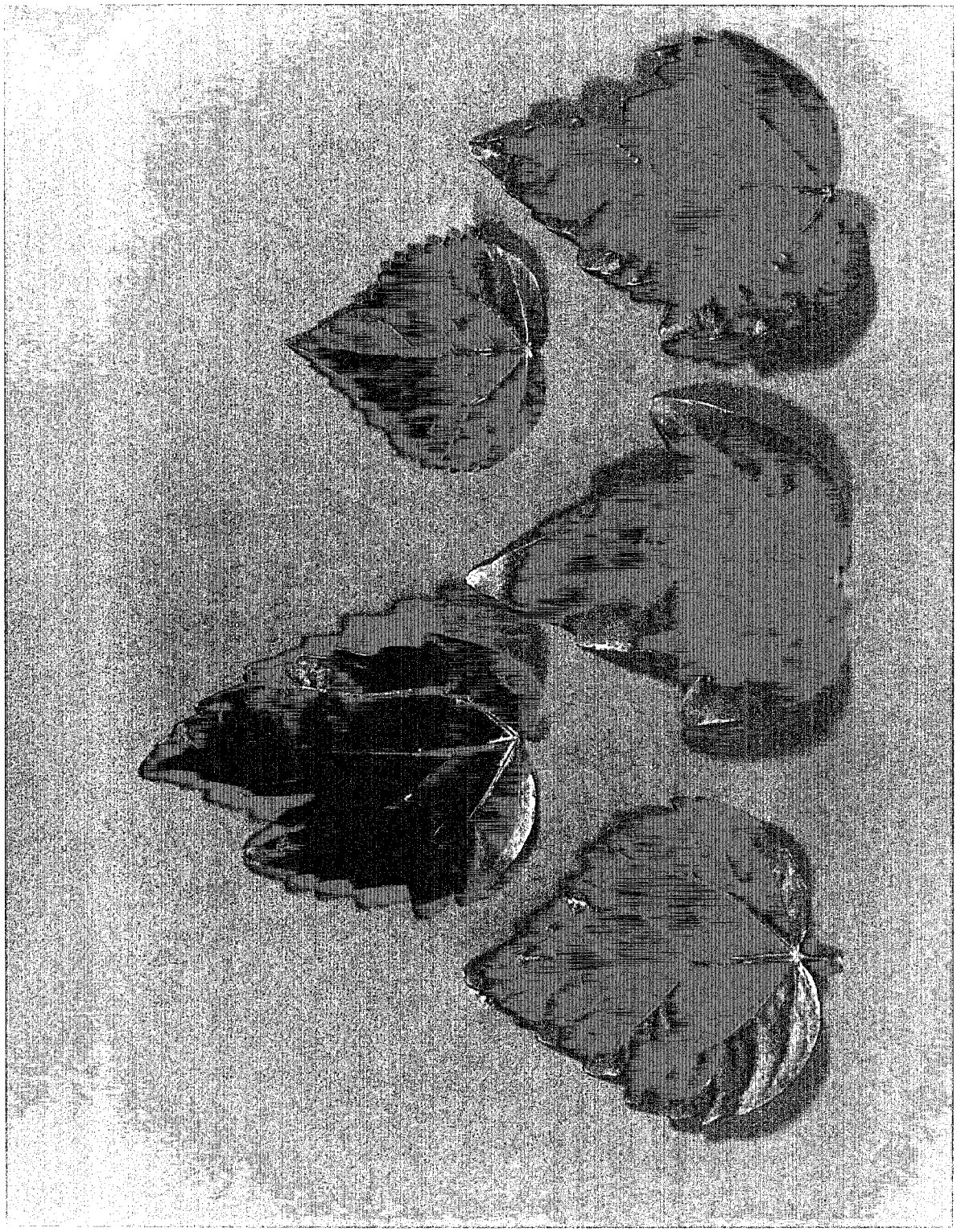

* * * * *